(12) United States Patent
Futamura (10) Patent No.: US 12,082,949 B2
(45) Date of Patent: Sep. 10, 2024

(54) SELECTION SUPPORT SYSTEM AND STORAGE MEDIUM

(71) Applicant: Konica Minolta, Inc., Tokyo (JP)

(72) Inventor: Hitoshi Futamura, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 299 days.

(21) Appl. No.: 16/896,848

(22) Filed: Jun. 9, 2020

(65) Prior Publication Data

US 2021/0007678 A1 Jan. 14, 2021

(30) Foreign Application Priority Data

Jul. 8, 2019 (JP) .................................. 2019-126618

(51) Int. Cl.
*A61B 5/00* (2006.01)
*G16H 30/20* (2018.01)
*G16H 30/40* (2018.01)

(52) U.S. Cl.
CPC ............ *A61B 5/743* (2013.01); *A61B 5/7435* (2013.01); *G16H 30/20* (2018.01); *G16H 30/40* (2018.01)

(58) Field of Classification Search
CPC ...... A61B 5/743; A61B 5/7435; G16H 30/20; G16H 30/40; G16H 40/63
USPC ......................................................... 600/301
See application file for complete search history.

(56) References Cited

U.S. PATENT DOCUMENTS

2008/0166070 A1 7/2008 Kariathungal et al.
2012/0123239 A1* 5/2012 Han .......................... A61B 5/08
600/407
2014/0275952 A1* 9/2014 Monroe .................. A61B 34/10
600/407
2016/0042146 A1* 2/2016 Douglass ............... G16H 50/70
705/3
2017/0360412 A1* 12/2017 Rothberg ............... A61B 8/065
(Continued)

FOREIGN PATENT DOCUMENTS

JP 2001-346042 A 12/2001
JP 2010-082277 A 4/2010
(Continued)

OTHER PUBLICATIONS

Office Action/Search Report mailed Dec. 13, 2022 for corresponding Japanese Application No. 2019-126618, with English translation.

*Primary Examiner* — James A Thompson
*Assistant Examiner* — Kim Thanh T Tran
(74) *Attorney, Agent, or Firm* — Lucas & Mercanti, LLP (57) ABSTRACT

A selection support system includes one or more hardware processors. A hardware processor among the one or more hardware processors obtains biological information of a subject. The hardware processor layers and accumulates, in an accumulator, input operation information about an input operation performed on the obtained biological information by a user. In response to obtaining new biological information, according to the input operation information accumulated in the accumulator, the hardware processor generates recommendation information that includes identification information identifying an application for analyzing the new biological information and additional information indicating a characteristic of the application.

17 Claims, 5 Drawing Sheets

(56) References Cited

U.S. PATENT DOCUMENTS

| | | | | |
|---|---|---|---|---|
| 2018/0330818 A1* | 11/2018 | Hsieh | ................. | G16H 40/60 |
| 2019/0333628 A1* | 10/2019 | Jo | ................. | G06F 3/0482 |
| 2020/0203003 A1* | 6/2020 | Yanagida | ............... | G16H 30/20 |
| 2021/0042916 A1* | 2/2021 | Zhang | ................. | A61B 6/50 |
| 2022/0245355 A1* | 8/2022 | Gnanasambandam | ................. | |
| | | | | G16H 10/20 |

FOREIGN PATENT DOCUMENTS

| | | |
|---|---|---|
| JP | 2012-133767 A | 7/2012 |
| JP | 2018-089157 A | 6/2018 |
| JP | 2018-130408 A | 8/2018 |

\* cited by examiner

SELECTION SUPPORT SYSTEM AND STORAGE MEDIUM

CROSS-REFERENCE TO RELATED APPLICATIONS

The entire disclosure of Japanese Patent Application No. 2019-126618 filed on Jul. 8, 2019 is incorporated herein by reference in its entirety.

BACKGROUND

Technological Field

The present disclosure relates to a selection support system and a storage medium.

Description of Related Art

Medical images, which include tomograms obtained with a computed tomography (CT) or a magnetic resonance imaging (MRI) and radiological images obtained with a radiological imaging apparatus called a flat panel detector (FPD), are typically stored in and managed with a server, and downloaded to clients to be viewable as desired (for example, see JP2010-82277A, JP2001-346042A).

A client needs to process a large amount of data to display medical images. Many techniques are proposed to smoothly perform the processing. In recent years, many applications for processing images so that users can smoothly interpret the images have been provided: for example, an application that extracts the position or shape of a lesion and shows thereof on an image; and an application that forms a three-dimensional image. When a user selects a desired application not only from applications originally loaded in a server or a client but from a market place presenting a list of applications, the client can display medical information including medical images on which desired processes have been performed.

SUMMARY

However, a user who has never used an application (who considers using an application) finds it difficult to select an appropriate application from the list of applications in the above-described system. It is further difficult to select an application in a market place where varieties of applications are presented.

A user who has already used an application also finds it difficult to select any other application, although the application that he/she has used may not be useful. The more applications the user uses, the more difficult it becomes to recognize correspondences between applications and processing results. This may lead to a misdiagnosis.

Objects of the present disclosure include providing a selection support system and a storage medium that can present an application(s) appropriate for a user.

To achieve at least one of the abovementioned objects, according to an aspect of the present invention, there is provided a selection support system that includes one or more hardware processors that include a hardware processor which: obtains biological information of a subject; layers and accumulates, in an accumulator, input operation information about an input operation performed on the obtained biological information by a user; and, in response to obtaining new biological information, according to the input operation information accumulated in the accumulator, generates recommendation information that includes identification information identifying an application for analyzing the new biological information and additional information indicating a characteristic of the application.

To achieve at least one of the abovementioned objects, according to another aspect of the present invention, there is provided a non-transitory computer-readable storage medium storing a program that causes a computer to: obtain biological information of a subject; layer and accumulate, in an accumulator, input operation information about an input operation performed on the obtained biological information by a user; and, in response to obtaining new biological information, according to the input operation information accumulated in the accumulator, generate recommendation information that includes identification information identifying an application for analyzing the new biological information and additional information indicating a characteristic of the application.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, one or more embodiments of the present invention will be described with reference to the drawings. However, the scope of the invention is not limited to the disclosed embodiments or drawings.

[Configuration of Selection Support System]

Figure 1:
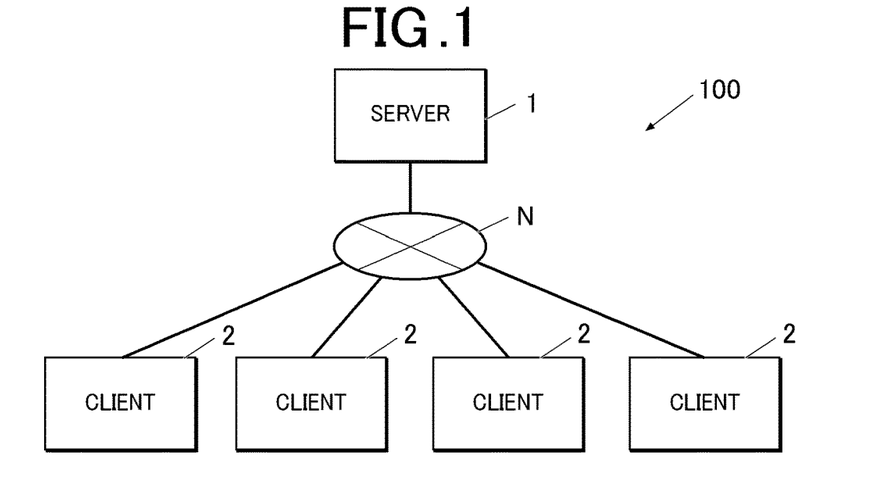
FIG. 1 is a block diagram showing a schematic configuration of a selection support system according to an embodiment of the present invention.

First, a configuration of a selection support system (hereinafter called system 100) according to this embodiment is described. FIG. 1 is a block diagram showing a schematic configuration of the system 100.

The system 100 according to this embodiment includes a server 1 and a client(s) 2, as shown in FIG. 1. The server 1 and the client 2 are not specifically limited in number.

The server 1 and the client 2 are connected to one another through a communication network N.

The server 1 is connected directly or through the communication network N to a not-shown modality (modalities), such as a computed tomography (CT), a magnetic resonance imaging (MRI), or a flat panel detector (FPD). The server 1 can obtain biological information, such as medical images of a subject generated by the modality, as data from the modality.

The client 2 receives medical image data from the server 1 and allows a user (e.g., doctor) to view (interpret) the medical image.

The modality is an apparatus conforming to the Digital Imaging and Communications in Medicine (DICOM) standard. The modality adds, as header information, various kinds of information (supplementary information) and a unique ID (UID) for identifying the image to a generated medical image, and sends the medical image to the server 1.

The supplementary information includes information on multiple items, for example, patient ID, name, sex, and birthdate of a patient, examination ID, examination time, examination condition (e.g., examined region, imaging direction, posture), examination note, type of modality, and/or image-interpretation request flag (ON/OFF).

[Server]

Figure 2:
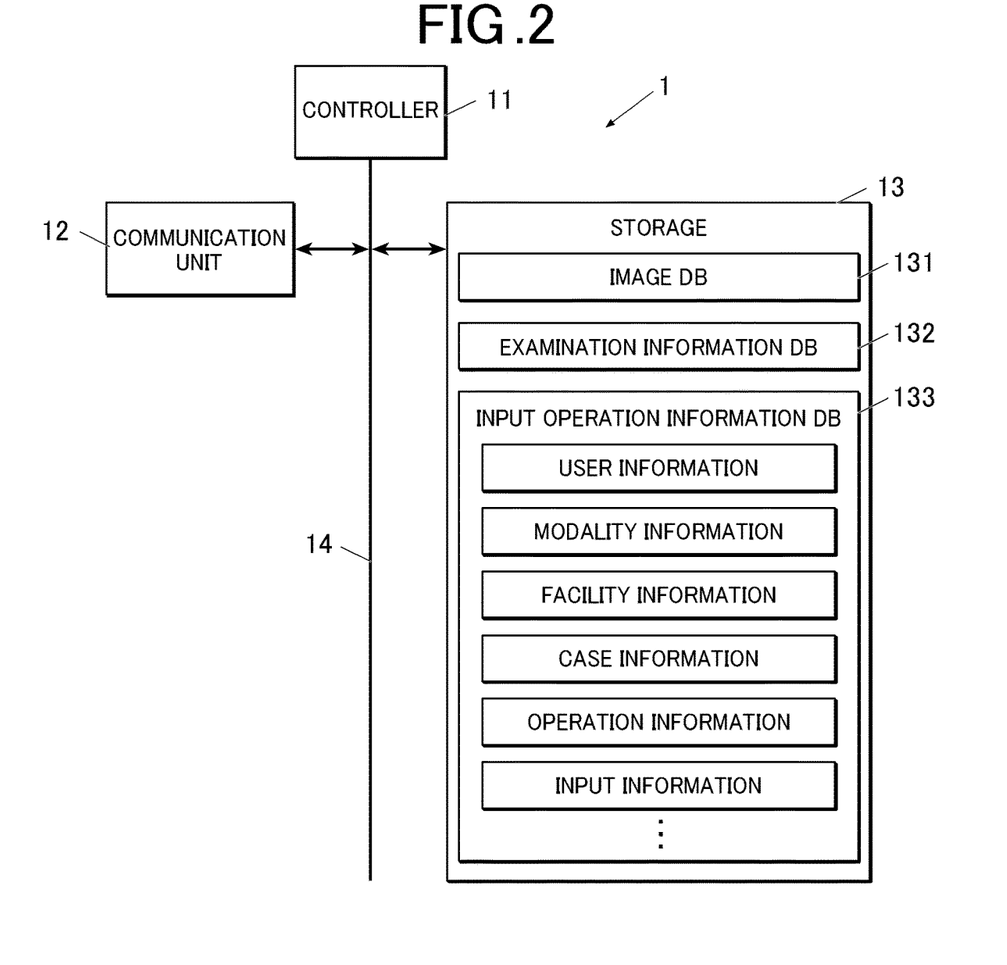
FIG. 2 is a block diagram showing a detailed configuration of a server.

Next, details of the server 1 are described. FIG. 2 is a block diagram showing a detailed configuration of the server 1.

The server 1 includes, as shown in FIG. 2, a controller 11 (obtainment unit, accumulation unit, generation unit, and display control unit) (hardware processor), a communication unit 12, and a storage 13 that are connected to each other through a bus 14.

The server 1 may be a cloud server prepared in a cloud environment, or the storage 13 alone may be managed in a cloud environment.

The server 1 may include a not-shown display and/or an operation unit and serve as an image processing apparatus or the like that can display medical images or perform various kinds of image processing.

The server 1 may be used alone or included in a system different from the selection support system, such as a Picture Archiving and Communication System (PACS).

The controller 11 includes a Central Processing Unit (CPU) and a Random Access Memory (RAM), and integrally controls processing operations of the components of the server 1. More specifically, the CPU reads various processing programs stored in the storage 13, loads the read programs into the RAM, and performs various processes in cooperation with the programs.

The communication unit 12 includes a network interface and exchanges data and so forth with an external apparatus (es) including the client 2 connected through the communication network N, such as a Local Area Network (LAN), a Wide Area Network (WAN), or the internet.

The storage 13 includes a Hard Disk Drive (HDD) and/or a nonvolatile semiconductor memory and stores various processing programs and parameters, files, and so forth required to perform the programs.

In this embodiment, the storage 13 stores: a web server program for causing a web browser to function as a web server that provides various web displays; a web application program that runs on the web server for providing medical images to a user of the client 2 through the web browser; and so forth.

The storage 13 includes an image data base (DB) 131, an examination information DB 132, and an input operation information DB 133 (accumulator).

The image DB 131 is a database for storing medical image data. The image DB 131 can store medical image data (original image data) sent from the modality and medical image data sent from the client 2 on which various kinds of image processing, such as image processing, have been performed.

The examination information DB 132 is a database for storing information on examinations (examination information) in which images of the medical image data stored in the image DB 131 have been taken. The examination information stored in the examination information DB 132 includes multiple items, such as examination ID, patient ID, name, sex, and birthdate of the patient as a subject, examination time, examination condition (e.g., imaged region, imaging direction, posture), examination note, type of modality, image-interpretation request flag (ON/OFF), status of image interpretation (not yet interpreted/interpreted), UID of a medical image taken in the examination, location where the medical image file is stored, and/or location where an image-interpretation report is stored.

The input operation information DB 133 is a database for layering and accumulating information on input operations (input operation information) performed by a user on an image of medical image data stored in the image DB 131.

The input operation information DB 133 stores input operation information by layers, such as: user information (e.g., depth intent, years of experience, qualified doctor information, age, sex, and log-in time); modality information (e.g., type and model specification); facility information (e.g., size of facility); case information (e.g., diagnosis result, case type, target region, elapsed years, age of a patient at the onset of the disease, disease severity, medical history, occurrence frequency, medical treatment information including a record of previous surgery, and effects of treatment); operation information (e.g., means of input, application selection result such as image analysis method, image processing application, and image processing function); saving format (e.g., text information or audio information); input information (e.g., contents of texts such as reports or memos, figures such as annotations or schemas, the number of times of inputs, and operation time).

In response to receiving medical image data from the modality, the controller 11 stores the received medical image data in the image DB 131. The controller 11 also combines header information of the received medical image data on an examination basis, and stores the information in the examination information DB 132.

In response to a request from the client 2, the controller 11 provides the medical image data stored in the image DB 131 to the client 2. When receiving input operation information on the medical image from the client 2, the controller 11 layers and stores the information in the input operation information DB 133.

The controller 11 obtains, from external apparatuses/systems such as a Hospital Information System (HIS), a Radiology Information System (RIS), or electronic medical records, related information that is associated with the received medical image data, and stores the related information as input operation information in the input operation information DB 133.

[Client]

Figure 3:
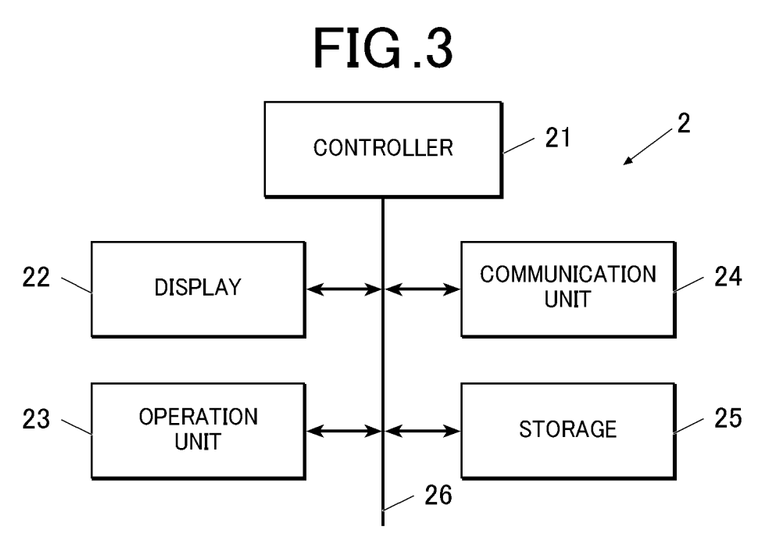
FIG. 3 is a block diagram showing a detailed configuration of a client.

Next, details of the client 2 are described. FIG. 3 is a block diagram showing a detailed configuration of the client 2.

The client 2 includes, as shown in FIG. 3, a controller 21 (display control unit) (hardware processor), a display 22, an operation unit 23, a communication unit 24, and a storage 25 that are connected to each other through a bus 26.

Examples of the client 2 include a desktop personal computer (PC) and a laptop PC. A smartphone, a tablet, a cellphone, or a personal digital assistant (PDA) may be used as well.

The controller 21 includes a CPU and a RAM, and integrally controls processing operations of the components of the client 2. More specifically, the CPU reads various processing programs stored in the storage 25, loads the read programs into the RAM, and performs various processes in cooperation with the programs.

The display 22 includes a monitor, such as a cathode ray tube (CRT) or a liquid crystal display (LCD), and displays various screens in accordance with instructions of display signals input by the controller 21.

For example, the display 22 displays an image-interpretation screen for interpreting medical images and a virtual market place (see FIG. 6) on the basis of display data of various web screens received from the server 1. In the virtual market place, a user can select an application to use for image interpretation.

The virtual market place is a term that symbolically means a virtual commercial space displayed on the display 22 and allowing users to trade one or more items. For example, in this embodiment, in displaying a new medical image, the virtual market place presents an application(s) determined to be useful for processing the new medical image. This allows the user to easily select an application.

The virtual market place is merely an example, and applications may not be commercial. A list of applications in the server or in the client may be displayed to be selectable.

The operation unit 23 includes a keyboard having various keys, a pointing device such as a mouse, and/or a touchscreen superposed on the display 22. The operation unit 23 outputs, to the controller 21, operation signals having been input according to key operations to the keyboard, operations of the mouse, or the position of a touching operation on the touchscreen.

The communication unit 24 includes a network interface and exchanges data and so forth with an external apparatus (es) including the server 1 connected through the communication network N, such as the LAN, the WAN, or the internet.

The storage 25 includes a Hard Disk Drive (HDD) and/or a nonvolatile semiconductor memory, and stores various processing programs and parameters, files, or the like required to perform the programs.

The storage 25 can store data, such as medical image data provided by the server 1 and processed medical image data generated when image processing or the like is performed on an image based on the medical image data. The storage 25 can also store input operation information accompanying with the processed medical image data.

The input operation information is sent to the server 1 at a predetermined timing under the control of the controller 21, and may be deleted after being sent. The processed medical image data may be sent to the server 1 along with the input operation information.

[Process Performed by Selection Support System]

Next, processes performed by the system 100 are described.

The processes performed by the system 100 in this embodiment are broadly classified into two processes: an information accumulation process for accumulating input operation information in the input operation information DB 133; and an information presentation process for presenting recommendation information, which is described later, to a user on the basis of the accumulated input operation information.

Hereinafter, details of these processes are described.

[Information Accumulation Process]

Figure 4:
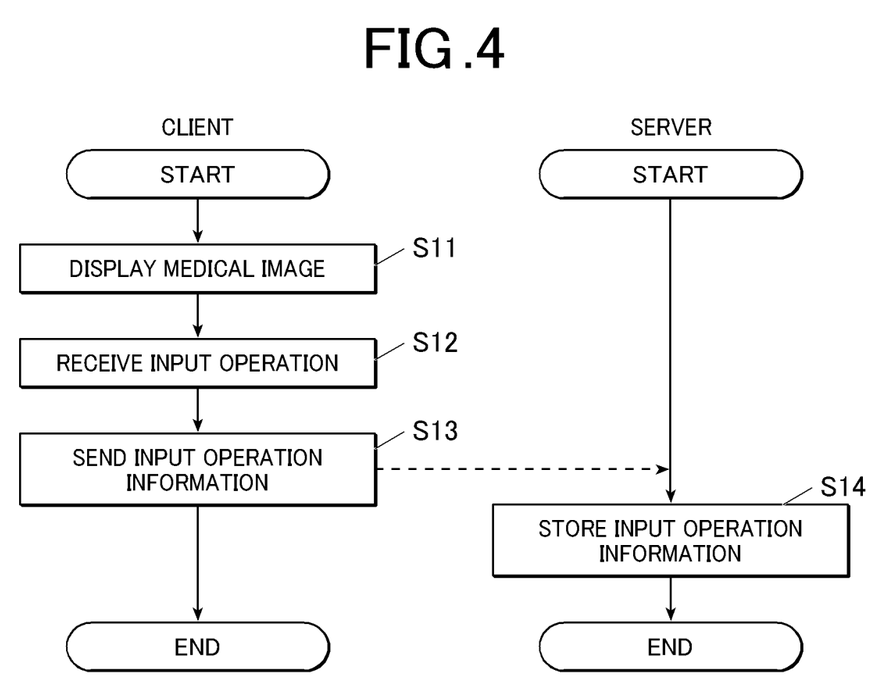
FIG. 4 is a flowchart showing an information accumulation process.

FIG. 4 is a flowchart showing steps of the information accumulation process.

First, the controller 21 of the client 2 causes the display 22 to display a medical image on the image-interpretation screen in accordance with an instruction operation performed by the user (Step S11).

Next, the controller 21 receives an input operation(s) performed on the medical image by the user operating the operation unit 23 (Step S12). This Step S12 is so-called image interpretation. In response to image interpretation, the controller 21 generates processed medical image data and accompanying input operation information, and stores thereof in the storage 25.

Examples of input operations by the user include designation of image analysis method, purpose of image analysis, and application, selection/entry of diagnosis results and findings, and entry of user information and image interpretation environments (e.g., date, size and name of facility).

Examples of input operation information generated as a result of input operations include: image analysis method, purpose of image analysis, application, and image processing function applied to the medical image; text or audio information on texts or audio having been input to the medical image; diagnosis result on the basis of the medical image; input operation time of each input operation; the number of times of input operations; time for loading the application and the image; user information; modality information; and facility information.

Further, as part of the input operation information, information related to the medical image or the user is generated according to the HIS, the RIS, or electronic medical records: for example, a medical history and elapsed years since the onset of the disease.

Next, the controller 21 sends, to the server 1, the input operation information received in above Step S2 at a predetermined timing (Step S13). The server 1 layers and stores the received input operation information in the input operation information DB 133 (Step S14).

Through the process described above, input operation information is accumulated in the input operation information DB 133.

[Information Presentation Process]

Figure 5:
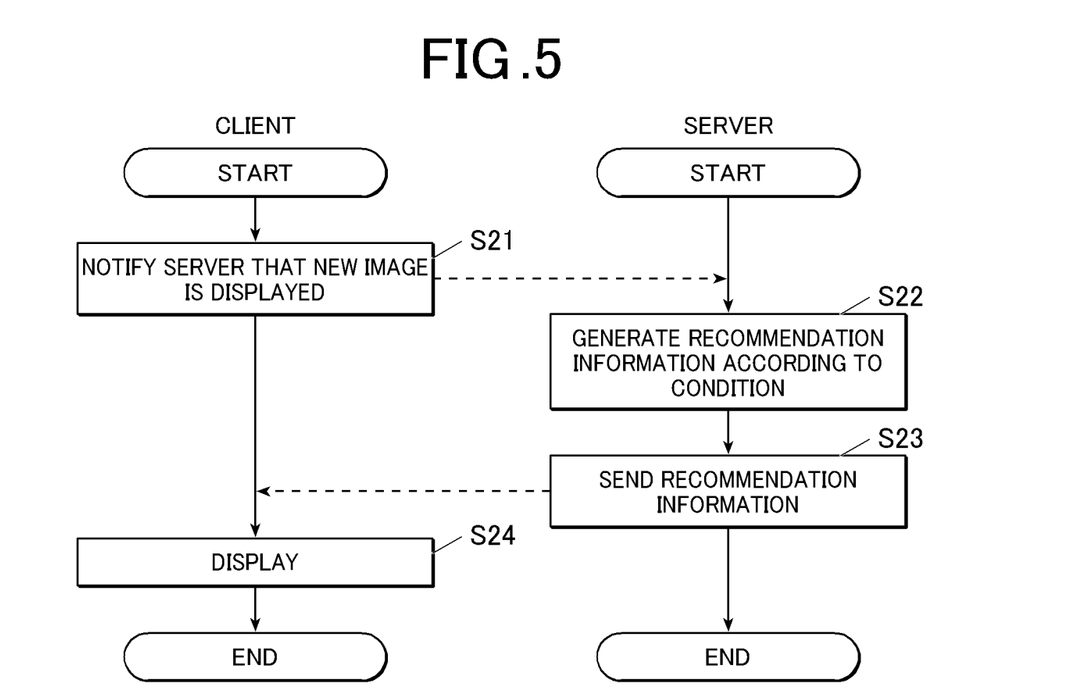
FIG. 5 is a flowchart showing an information presentation process.

FIG. 5 is a flowchart showing steps of the information presentation process.

First, in displaying a new medical image that has never been displayed by the client 2, the controller 21 of the client 2 notifies the server 1 that the new medical image is displayed in accordance with an instruction operation(s) by the user (Step S21).

For example, when the user operates a reading-new-image button (not illustrated) on the image-interpretation screen and specifies condition information on the image to be displayed (e.g., patient name, imaged date, and modality type), the controller 21 sends notification signals including the condition information to the server 1. The condition information may include information on the user performing operations, as well as information on the image.

When receiving the notification signals including the condition information, the controller 11 of the server 1 identifies, on the basis of the condition information, the image to be displayed by the client 2. The controller 11 selects an application(s) and information appropriate for (i.e., determined to be available for processing) the identified image according to input operation information accumulated in the input operation information DB 133. The controller 11 then generates recommendation information including: identification information for identifying the application; and additional information indicating characteristics of the application (Step S22).

More specifically, when the selected image is a chest image, applications are narrowed down to one or more applications for obtaining analysis results on the chest, and an icon(s) for identifying the narrowed application(s) is generated as identification information. The identification information may not be in a form of an icon but may be in any form, as long as the application is distinguishable.

When applications are narrowed down to a plurality of applications, it may be preferable to prioritize the narrowed applications according to a predetermined condition. For example, among the narrowed applications, an application appropriate for case information recorded in a past diagnosis report of the patient of the identified image may be highly prioritized.

For each of the narrowed applications, related information is extracted from input operation information to generate additional information. The additional information indicates, for example, the purpose of using the application (purpose of image analysis), frequency in combination of the case and the application, the number of users having used the application, or the number of times that the user has used the application.

As the additional information, information on the number of times of operations, operation time in using the application, or time required for loading may be generated.

In forming an image that is supposed to be used at conferences or academic meetings, the following may be extracted and included in additional information: difference between (i) frequency of selection of the application in the hospital alone to which the user belongs and (ii) frequency of selection of the application in hospitals including the above hospital and other hospitals; or comments on the use of the application by prominent users only, as well as the information on applications having been used so far.

Next, the controller 11 sends the new medical image data (original image data) and the generated recommendation information to the client 2 (Step S23). The controller 21 of the client 2 causes the display 22 to display the virtual market place and the new medical image (Step S24).

Figure 6:
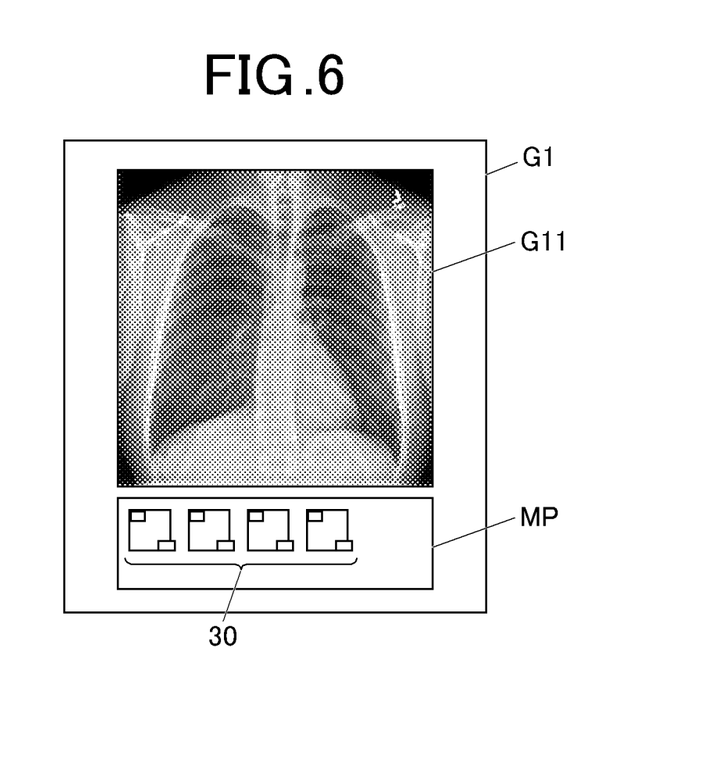
FIG. 6 exemplifies a display screen of a virtual market place.

FIG. 6 exemplifies a display screen G1 displayed on the display 22 in above-described Step S24.

As shown in FIG. 6, the display screen G1 includes an image display section G11 on which a new medical image (original image) is displayed and the virtual market place MP.

The virtual market place MP displays recommendation information 30 showing one or more applications. The virtual market place MP may display purchased applications only, and in such a case, may not display recommendation information.

FIGS. 7A to 7D are diagrams for explaining details of the recommendation information 30.

As described above, the recommendation information 30 includes an icon 31 that makes an application identifiable and additional information 32 that indicates characteristics of the application.

Figure 7A:
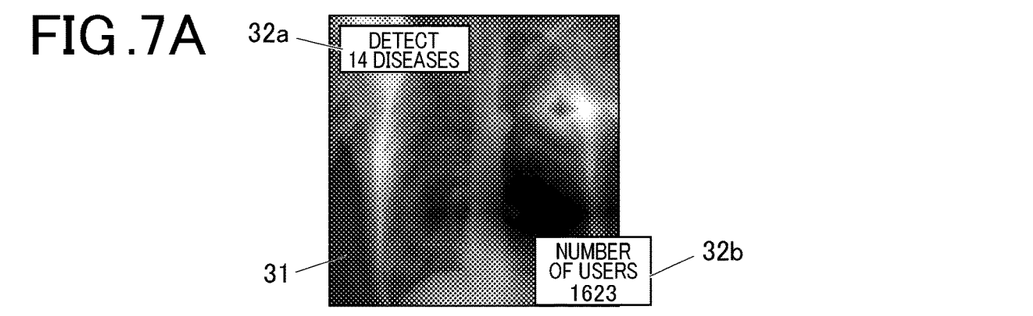
FIGS. 7A to 7D are diagrams for explaining icons shown in the virtual market place.

As shown in FIG. 7A and other figures, a reduced-size image of an image to be generated with the application is used as an icon 31, for example.

The additional information 32 includes text information 32a in a form of a label showing the purpose of using the application (purpose of image analysis) or a comment by a user, for example. The additional information 32 also includes numeric information 32b, such as frequency in combination of the case and the application, the number of users using the application, the number of times that the application has been used, the number of times of operations or operation time in using the application, or time required for loading.

The additional information 32 may include only either text information 32a or numeric information 32b.

Figure 7B:
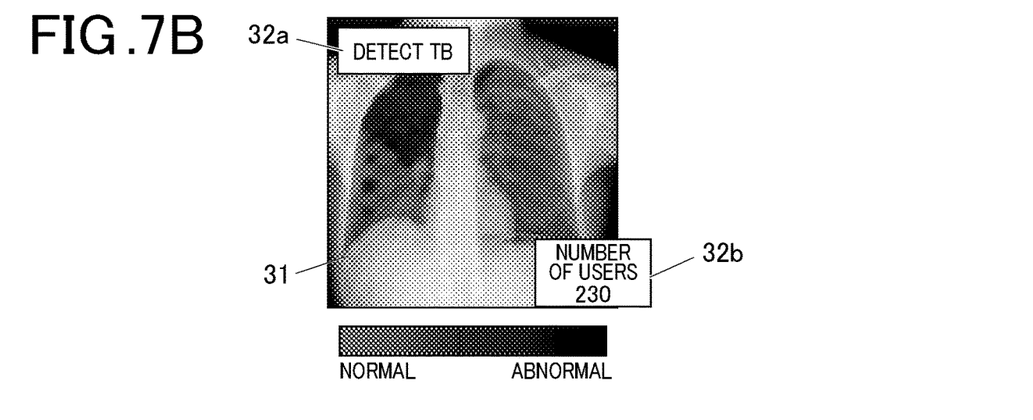

FIGS. 7A, 7B each exemplify a case where additional information 32 includes text information 32a indicating functions of the application and numeric information 32b indicating the number of users using the application.

Figure 7C:
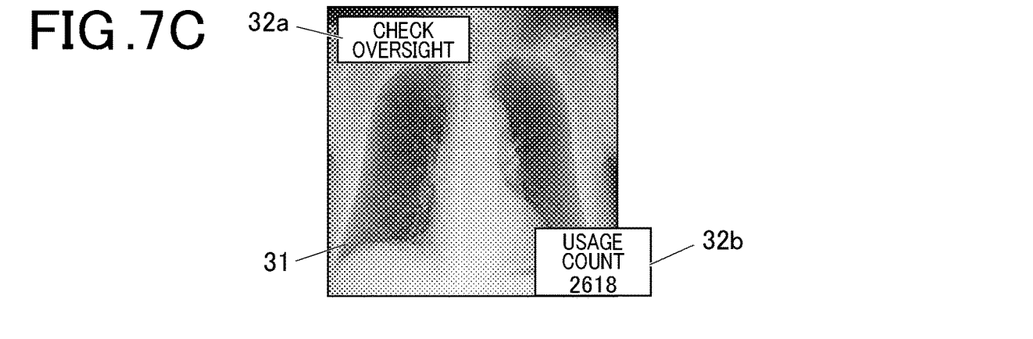

FIG. 7C exemplifies a case where additional information 32 includes text information 32a indicating how the application has been used by users and numeric information 32b indicating the number of times that the application has been used.

Figure 7D:
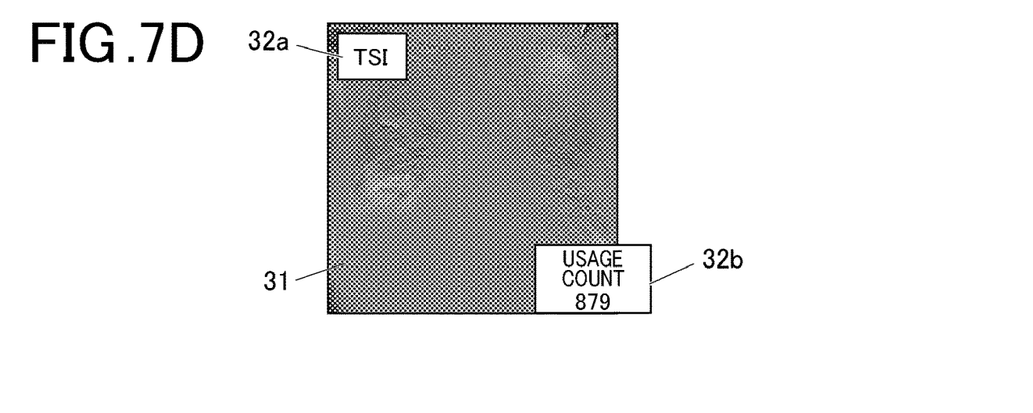

As shown in FIG. 7D, text information 32a may be information included in a DICOM tag.

The virtual market place MP displays one or more icons 31 that indicate one or more applications narrowed for the new medical image in the priority order. This allows a user to select an application easily.

Further, additional information 32 includes frequency in combination of the case and the application, the number of users having used the application, or the number of times that the user has used the application. This allows the user to select an application more easily.

Further, when additional information 32 includes the number of times of operations or operation time in using the application, or time required for loading additional information 32, the user can easily select an application(s) that requires less time.

Further, use of new applications may be promoted when additional information 32 includes: difference between (i) frequency of selection of the application in the hospital alone to which the user belongs and (ii) frequency of selection of the application in hospitals including the above hospital and other hospitals; or comments on the use of the application by prominent users only.

Thus, presentation of recommendation information 30 in displaying a new medical image allows the user to easily select an application.

As described above, in the embodiment, the client 2 obtains recommendation information along with new medical image data from the server 1 and displays the recommendation information and the new medical image. However, the client 2 may obtain recommendation information alone from the server 1 and display thereof before a new medical image is taken.

For example, the imaging date is set in the future, and condition information that specifies a modality name(s), a diagnosis region(s), a department in charge, or the like is sent to the server 1. The server 1 can generate recommendation information by selecting an application(s) and information that meet the condition according to input operation information accumulated in the input operation information DB 133.

Figure 8:
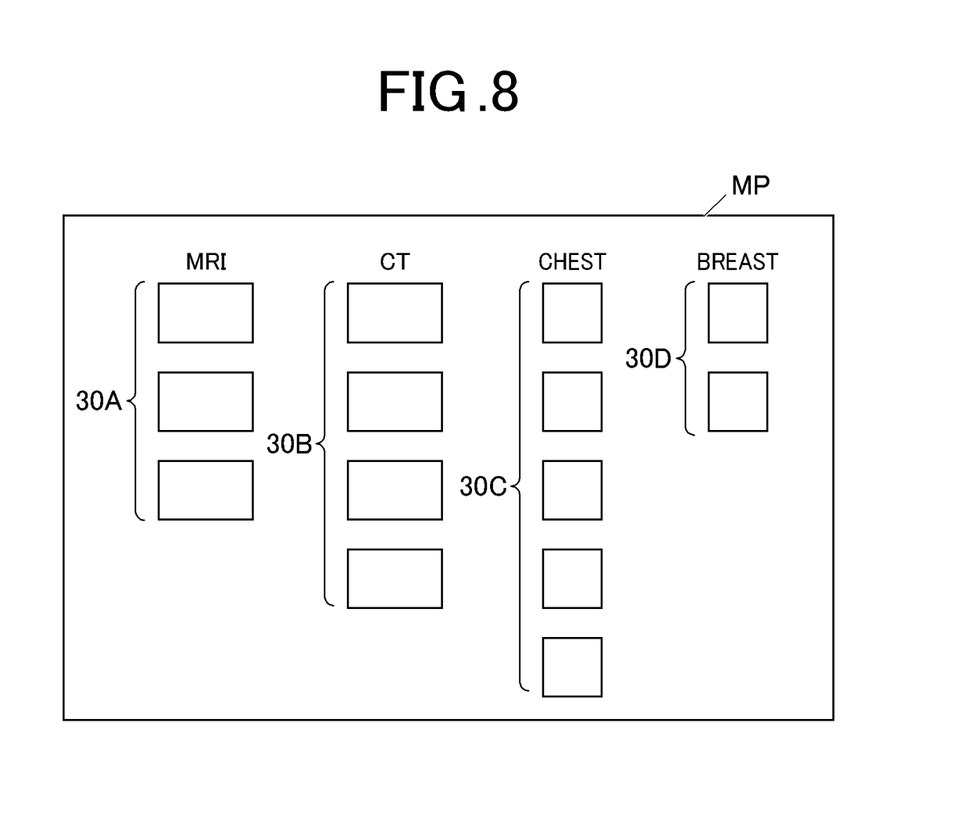
FIG. 8 exemplifies a display screen of the virtual market place.

In this case, applications recommended according to the condition are listed and displayed as shown in FIG. 8, and the client 2 can wait for image data to be sent. FIG. 8 exemplifies a case where pieces of recommendation information 30A to 30D are displayed according to conditions in which modality names (MRI and CT) and diagnosis regions (chest and breast) are specified.

Advantageous Effects of Embodiments

As described above, according to the embodiment, the controller 11 obtains image information (biological information) of a subject imaged, and layers and accumulates, in the input operation information DB 133, input operation information about an input operation performed on the obtained image information by a user. In response to obtaining new image information, according to the accumulated input operation information, the controller 11 generates recommendation information 30 that includes: an icon(s) 31 identifying an application for analyzing the new image information; and additional information 32 indicating a characteristic(s) of the application.

Thus, the controller 11 can generate recommendation information 30 according to the accumulated information. With the recommendation information 30, the controller 11 can present an application(s) appropriate for the user.

Further, according to the embodiment, the controller 11 and the controller 21 cause the display 22 to display the generated recommendation information 30.

This allows the user to recognize and select an appropriate application.

Further, according to the embodiment, the controller 11 and the controller 21 cause the display 22 to display the recommendation information 30 along with the new image information.

This improves usability.

Further, according to the embodiment, the controller 11 generates the recommendation information 30 that includes: icons 31 of applications for which a priority order is determined according to a predetermined condition; and the additional information 32 on each of the applications. The controller 11 and the controller 21 cause the display 22 to display the recommendation information 30 such that the icons 31 of the applications are displayed in the priority order.

This allows the user to select an appropriate application more easily.

Further, according to the embodiment, the input operation information includes at least one of user information, modality information, facility information, case information, operation information, or input information.

That is, the recommendation information 30 is generated on the basis of at least one of user information, modality information, facility information, case information, operation information, or input information.

[Others]

In the above embodiment, recommendation information is selected on the basis of image information of a subject imaged. However, the present invention is also applicable to biological information other than image information.

Further, there is one input operation information DB 133 in the above embodiment. However, there may be two or more input operation information DBs 133. In such a case, an application(s) and information can be selected for each of the input operation information DBs 133. The results of the selections may be presented and compared, and the comparison result may be presented.

Further, one of clients may have functions as a server. That is, the information accumulation process and the information presentation process may be performed under the control of the client.

Although embodiments of the present invention have been described and illustrated in detail, the disclosed embodiments are made for purposes of illustration and example only and not limitation. The scope of the present invention should be interpreted by terms of the appended claims.

What is claimed is:

1. A selection support system comprising one or more hardware processors that include a hardware processor which:
   obtains biological information of a subject, the biological information including a medical image;
   layers and accumulates, in an accumulator, input operation information about an input operation performed on the obtained medical image by a user; and
   in response to obtaining new biological information including a new medical image, according to the input operation information accumulated in the accumulator, generates recommendation information that includes identification information identifying an application for interpreting the new medical image and
   additional information indicating a characteristic of the application selected from the group consisting of a frequency in combination of a case of the biological information and the application, a number of users using the application, a number of times that the application has been used, number of times of operations or operation time in using the application, or time required for loading, a function of the application, and how the application has been previously used; and
   wherein at least one hardware processor among the one or more hardware processors causes a display to display the recommendation information in groupings according to condition in which at least one of modality names and diagnosis regions are specified.

2. The selection support system according to claim 1, wherein the at least one hardware processor causes the display to display the recommendation information along with the new medical image.

3. The selection support system according to claim 1, wherein
   the hardware processor generates the recommendation information that includes
   the identification information on applications each of which is the application and for which a priority order is determined according to appropriateness for a predetermined condition and
   the additional information on each of the applications, and
   the at least one hardware processor causes the display to display the recommendation information such that the identification information on the applications is displayed in the priority order.

4. The selection support system according to claim 1, wherein the medical image is image information obtained by imaging the subject.

5. The selection support system according to claim 1, wherein the input operation information includes at least one among user information, modality information, facility information, case information, operation information, and input information.

6. The selection support system according to claim 1, comprising accumulators each of which is the accumulator, wherein the hardware processor generates the recommendation information for each of the accumulators.

7. The selection support system according to claim 1, wherein the input operation information includes at least one of user information, modality information regarding a modality with which the biological information was obtained, facility information, and case information of the subject.

8. The selection support system according to claim 1, wherein the at least one hardware processor causes the display to display the application of the generated recommendation information to be selectable.

9. The selection support system according to claim 1, wherein the recommendation includes information on applications, each of which is the application, and the additional information on each of the applications, wherein the at least one hardware processor causes the display to display a list of the applications to be selectable.

10. The selection support system according to claim 1, wherein
the identification information is an icon that makes the application identifiable and the additional information is presented as a label including text information or numeric information on the icon.

11. The selection support system according to claim 10, wherein
the icon is a reduced-size image of an image to be generated with the application.

12. The selection support system according to claim 1, wherein the additional information includes a frequency of a case of the biological information and the application.

13. The selection support system according to claim 1, wherein the additional information includes text information indicating at least one of a function of the application and how the application has been previously used.

14. The selection support system according to claim 13, wherein the additional information is information included in a DICOM tag.

15. The selection support system according to claim 1, wherein the additional information includes a difference between (i) frequency of selection of the application in the hospital alone to which the user belongs and (ii) frequency of selection of the application in hospitals including the above hospital and other hospitals.

16. The selection support system according to claim 1, wherein the additional information includes comments on the use of the application by prominent users.

17. A non-transitory computer-readable storage medium storing a program that causes a computer to:
obtain biological information of a subject, the biological information including a medical image;
layer and accumulate, in an accumulator, input operation information about an input operation performed on the obtained medical image by a user; and
in response to obtaining new biological information including a new medical image, according to the input operation information accumulated in the accumulator, generate recommendation information that includes identification information identifying an application for interpreting the new medical image and
additional information indicating a characteristic of the application selected from the group consisting of a frequency in combination of a case of the biological information and the application, a number of users using the application, a number of times that the application has been used, number of times of operations or operation time in using the application, or time required for loading, a function of the application, and how the application has been previously used; and
cause a display to display the recommendation information in groupings according to conditions in which at least one of modality names and diagnosis regions are specified.

* * * * *